(12) United States Patent
Ronvig

(10) Patent No.: US 6,368,336 B1
(45) Date of Patent: Apr. 9, 2002

(54) DEVICE FOR SOFT TISSUE MODELING AND COAGULATING SOFT TISSUE

(75) Inventor: Jorn Ronvig, Hedensted (DK)

(73) Assignee: Ronvig A/S, Daugard (DK)

( * ) Notice: Subject to any disclaimer, the term of this patent is extended or adjusted under 35 U.S.C. 154(b) by 0 days.

(21) Appl. No.: 09/416,300

(22) Filed: Oct. 12, 1999

(51) Int. Cl.$^7$ ............................................... A61B 17/14
(52) U.S. Cl. ...................................................... 606/180
(58) Field of Search .............................. 606/180, 170, 606/167, 184, 28, 45, 51, 49, 32, 27; 128/898

(56) References Cited

U.S. PATENT DOCUMENTS

| | | | |
|---|---|---|---|
| 4,197,645 A | | 4/1980 | Scheicher |
| 4,221,222 A | | 9/1980 | Detsch |
| 4,259,069 A | | 3/1981 | Lustig |
| 4,723,911 A | | 2/1988 | Kurtz |
| 4,738,248 A | | 4/1988 | Ray |
| 4,765,331 A | * | 8/1988 | Petruzzi et al. ............... 606/40 |
| 4,778,471 A | | 10/1988 | Bajpai |
| 5,192,279 A | | 3/1993 | Samuels et al. |
| 5,269,785 A | | 12/1993 | Bonutti |
| 5,295,990 A | * | 3/1994 | Levin ........................... 606/49 |
| 5,344,420 A | * | 9/1994 | Hilal et al. .................... 606/28 |
| 5,388,980 A | | 2/1995 | Kijima et al. |
| 5,403,317 A | | 4/1995 | Bonutti |
| 5,683,249 A | | 11/1997 | Ibsen et al. |
| 5,694,951 A | | 12/1997 | Bonutti |
| 5,720,894 A | | 2/1998 | Neev et al. |
| 5,725,370 A | | 3/1998 | Himeno et al. |
| 5,785,522 A | | 7/1998 | Bergstrom et al. |
| 5,801,110 A | | 9/1998 | Pugliesi et al. |
| 5,823,774 A | | 10/1998 | Abbott et al. |
| 5,839,895 A | | 11/1998 | Fishburne, Jr. |
| 5,871,469 A | | 2/1999 | Eggers et al. |
| 5,879,362 A | | 3/1999 | Amann et al. |
| 5,925,412 A | | 7/1999 | Raghavan et al. |
| 5,935,131 A | | 8/1999 | Bonutti |

* cited by examiner

*Primary Examiner*—Kevin Truong
(74) *Attorney, Agent, or Firm*—Merchant & Gould P.C.

(57) ABSTRACT

The invention relates to a device preferably in the form of a ceramic trimmer that is useful in treating soft tissue such as gingival tissue in an individual. The device Is capable of heat coagulating the soft tissue when the device in rotary motion is contacting the soft tissue. The device is preferably used in the area of therapy or surgery carried out on the human or animal body.

49 Claims, 1 Drawing Sheet

DEVICE FOR SOFT TISSUE MODELING AND COAGULATING SOFT TISSUE

TECHNICAL FIELD OF THE INVENTION

Figure 1:
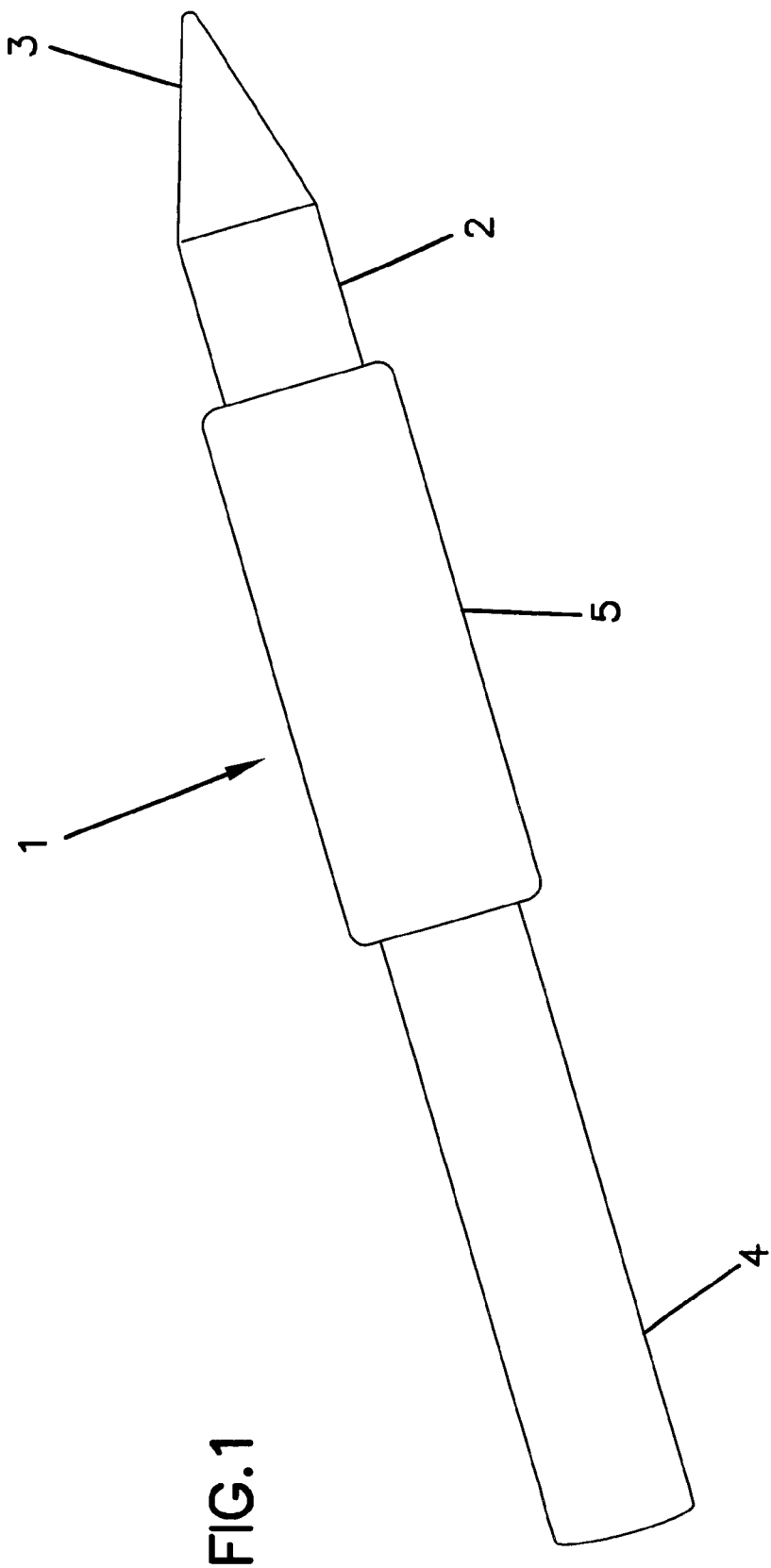

The invention relates to a device preferably in the form of a ceramic trimmer that is useful in treating soft tissue such as gingival tissue in an individual. The device is capable of soft tissue modelling and heat coagulating the soft tissue when the device in rotary motion is contacting the soft tissue. The device is preferably used in the area of therapy or surgery carried out on the human or animal body.

BACKGROUND OF THE INVENTION

The prior art discloses drilling devices and dental tips for treatment of hard tissue such as bone and various non-vascular tissues such as cartilage. Such tissues essentially do not contain any body fluids and heat coagulation is therefore not an issue to be considered when treating these non-vascular tissues. The prior art neither discloses treatment of soft body tissue that results in heat coagulation of said soft tissue, nor does the prior art disclose a method of treatment that leads to an improved hemostasis by means of heat coagulation during soft tissue treatment.

U.S. Pat. No. 5,269,785 relates to a percutaneous tissue removal apparatus for cutting hard tissue such as for example bone, cartilage and fetal tissue. Heat coagulation of soft tissue or hemostasis of soft tissue is not disclosed and does not occur in a treatment of hard tissue in accordance with the disclosure of the patent.

U.S. Pat. No. 5,725,370 discloses a dental tip for use in periodental treatment such as a method of removing dental calculus. The dental tip is not for use with soft tissue, and a heat coagulating effect of soft tissue is not disclosed.

SUMMARY OF THE INVENTION

In one aspect of the present invention there is provided a device for treatment of soft tissue, said device comprising a distal end portion comprising a heat-insulating material and a proximal end portion in the form of a non-flexible drill shaft capable of being in operational contact with a power source for generating a rotary motion of said distal end portion, said rotary motion resulting in a heat coagulation of said soft tissue being contacted under practical circumstances by at least said rotating distal end comprising said heat-insulating material.

The device according to the invention is particularly useful in the field of dentistry and provides a means for improving various forms of treatment including gingival tissue modelling, removing mucous membranes, mucous lined tissues and hyper-plastic gingival tissue, exposing a tooth at least partly covered by a mucous membrane or mucous lined tissue, laceration of interradiculary granulation tissue, exposing an intraosseous implant or part thereof, and poche opening in connection with making a dental impression.

Furthermore, due to the frictional energy released when rotating the device a cutting effect is obtained in addition to the coagulation. Thus, the device is suitable for use in treatments wherein the combined cutting and coagulation of soft tissues are desired.

The device is capable of being fitted in any conventional dentistry apparatus useful for performing a drilling action. In particular the device is capable of being fitted into a friction grip shaft, such as shaft of a diameter of 1.6 mm. In addition to resulting in an improved heat coagulation and/or hemo- stasis of soft tissue being contacted by the rotating distal end comprising the heat-insulating material, the device is also useful in achieving even and well modelled surfaces of a wound as well as an improved hemostasis. The device also represents an improvement when it is desirable to produce or clean a poche opening e.g. in connection with a dental impression.

In one aspect the invention provides a method of heat coagulating soft tissue, said method comprising the steps of
  i) providing a device according to the present invention,
  ii) providing an individual in need of soft tissue treatment,
  iii) contacting said soft tissue by at least said distal end portion of said device, and
  iv) heat coagulating said soft tissue by means of said rotary motion of at least said distal end portion.

In yet another aspect there is provided a method of removing or modelling gingival tissue, said method comprising the steps of
  i) providing a device according to the present invention,
  ii) providing an individual in need of gingival tissue removal,
  iii) contacting said gingival tissue by at least said distal end portion of said device,
  iv) removing or modelling said gingival tissue by means of said rotary motion of at least said distal end portion of said device, said rotary motion further resulting in heat coagulating said gingival tissue being contacted under practical circumstances by at least said rotating distal end.

The above method may also pertain to removing gingival tissue in the form of hyperplastic gingival tissue.

Yet another aspect of the present invention pertains to a method of lacerating interradiculary granulation tissue, said method comprising the steps of
  i) providing a device according to the present invention,
  ii) providing an individual in need of interradiculary granulation tissue laceration,
  iii) contacting said granulation tissue with at least said distal end portion of said device, and
  iv) lacerating said interradiculary granulation tissue by means of said rotary motion of at least said distal end portion of said device, said rotary motion further resulting in heat coagulating said interradiculary granulation tissue being contacted under practical circumstances by at least said rotating distal end.

In a further aspect there is provided a method of exposing a tooth or an intraosseous implant, or part thereof, at least partly covered by a mucous membrane or mucous lined tissue, said method comprising the steps of
  i) providing a device according to the present invention,
  ii) providing an individual in need of exposure of a tooth at least partly covered by a mucous membrane or mucous lined tissue,
  iii) contacting said mucous membrane or mucous lined tissue with said distal end portion of said device,
  iv) exposing said tooth at least partly covered by a mucous membrane or mucous lined tissue by means of said rotary motion of said distal end portion of said device, said rotary motion resulting in a heat coagulation of said mucous membrane or mucous lined tissue being contacted under practical circumstances by at least said rotating distal end.

In a yet further aspect there is provided a method of cleaning a poche e.g. when making a dental impression, said method comprising the steps of i) providing a device according to the present invention,
ii) providing an individual in need of poche cleaning,
iii) contacting said poche with said distal end portion of said device,
iv) cleaning said poche by means of said rotary motion of said distal end portion of said device, said rotary motion resulting in a heat coagulation of soft tissue comprised in said poche being contacted under practical circumstances by at least said rotating distal end.

In a further aspect there is provided the use of a ceramic drill tip in the manufacture of a device for treatment of soft tissue, said device comprising a distal end portion comprising said ceramic drill tip and a proximal end portion in the form of a non-flexible drill shaft capable of being in operational contact with a power source for generating a rotary motion of at least said distal end portion, said rotary motion resulting in a heat coagulation of said soft tissue being contacted under practical circumstances by at least said rotary distal end comprising said ceramic drill tip.

There is also provided the use of a ceramic drill tip in the manufacture of a device for treatment of soft tissue, said device comprising a distal end portion comprising said ceramic drill tip and a proximal end portion in the form of a non-flexible drill shaft capable of being in operational contact with a power source for generating a rotary motion of at least said distal end portion, said rotary motion resulting in hemostasis of said soft tissue being contacted under practical circumstances by at least said rotary distal end comprising said ceramic drill tip.

DRAWINGS

FIG. 1 shows a device according to the invention

DETAILED DESCRIPTION OF THE INVENTION

The device according to the present invention is useful in treating soft body tissue in a human or animal. The device comprises a distal end portion comprising a heat-insulating material. The heat insulating material may also be termed heat resistant. Irrespective of which term is being used, the material is characterised by the property of being essentially unable to conduct energy in the form of heat generated for example when soft tissue is contacted by at least said distal end portion in rotary motion. As a result of the heat insulating nature of the material, the generated heat is instead directed towards the surface of the soft tissue where it results in heat coagulation and an improved hemostasis.

The device according to the invention also comprises a proximal end portion in the form of a non-flexible drill shaft capable of being in operational contact with a power source. The operable connection to the power source results in a rotary motion of at least said distal end portion. The rotary motion of at least said distal end portion is sufficient to generate the desired heat coagulation of the soft tissue that is contacted under practical circumstances by at least the distal end comprising the heat-insulating material.

One effect of achieving heat coagulation of said soft tissue is that the outflow of fluids from said soft tissue is being reduced and/or essentially eliminated during or following a treatment of said soft tissue that involves contacting said tissue with at least said distal end portion comprising said heat insulating material. It is preferred that said heat coagulation essentially eliminates the outflow of fluids from said soft tissue.

The fluids may be any serum fluid present in said tissue including fluids comprising blood. When the fluids comprise blood the heat coagulation results in an improved hemostasis by reducing and/or at least essentially eliminating the outflow of blood from said treated soft tissue. The soft tissue capable of being contacted by at least said distal end portion of the device according to the invention is any soft human or animal tissue including tissue comprising vascular tissue, such as soft tissue, comprising mucosal tissue, such as gingival tissue. In one preferred embodiment the soft tissue essentially consists of gingival tissue.

The heat insulating material according to the invention is preferably selected from the group consisting of a ceramic material and a cermet in the form of an alloy comprising a heat-insulating compound and a metal. The heat-insulating compound may also be referred to as a heat-resistant compound. Both the ceramic material and the cermet is characterised by being heat-insulating. Accordingly, both the ceramic material and the cermet will direct the generated heat towards the surface of the soft tissue.

It is preferred that the heat insulating material either comprises a ceramic material or essentially consists of a ceramic material. It is preferred that the heat insulating material consists of a ceramic material. The distal end portion comprising said heat-insulating material is sterilizable and/or disposable.

The distal end portion comprising said heat-insulating material preferably consisting of a ceramic material preferably has a thermal conductivity that is not substantially greater than that of a typical ceramic material, and more preferably, said distal end portion comprising said heat-insulating material is thermally non-conductive or essentially non-conductive.

The distal end portion comprising said heat-insulating material preferably consisting of a ceramic material preferably has a Rockwell C hardness of at least about 20, such as about 22, for example about 24, such as about 26, for example about 28, such as about 30, for example about 32, such as about 34, for example about 36, such as about 38, for example about 40, such as about 42, for example about 44, such as about 46, for example about 48, such as about 50, for example about 52, such as about 54, for example about 56, such as about 58, for example about 60, such as about 62, for example about 64, such as about 66, for example about 68, such as about 70, for example about 72, such as about 74, for example about 76, such as about 78, for example about 80, such as about 82, for example about, 84, such as about 86, for example about 88, such as about 90, for example about 95, such as about 100, for example about 105, such as about 110, for example about 115, such as about 120, for example about 130, such as about 140, for example about 150 and preferably a Rockwell C hardness of less than about 200.

The distal end portion comprising said heat-insulating material preferably consisting of a ceramic material is preferably electrically non-conductive. This is achieved under practical circumstances when the electrical resistivity of said heat-insulating material is preferably at least about $5 \times 10^2$ ohm/cm$^2$, for example about $10^3$ ohm/cm$^2$, such as about $5 \times 10^3$ ohm/cm$^2$, for example about $10^{4 \text{ ohm/cm2}}$, such as about $5 \times 10^4$ ohm/cm$^2$, for example about $10^5$ ohm/cm$^2$, such as about $5 \times 10^5$ ohm/cm$^2$, for example about $10^6$ ohm/cm$^2$, such as about $5 \times 10^6$ ohm/cm$^2$, for example about $10^7$ ohm/cm$^2$, such as about $5 \times 10^7$ ohm/cm$^2$.

In one embodiment, the ceramic material is preferably selected from the group consisting of a carbide of a transition metal of group IVa of the Periodic Table, a carbide of a transition metal of group Va of the Periodic Table, a nitride of a transition metal of group IVa of the Periodic Table, a nitride of a transition metal of group Va of the Periodic Table, a carbonitride of a transition metal of group IVa of the Periodic Table, a carbonitride of a transition metal of group Va of the Periodic Table, an oxide of a transition metal of group IVa of the Periodic Table, and an oxide of a transition metal of group Va of the Periodic Table, including any mixture thereof.

The transition metals of group IVa of the Periodic Table comprise Ti (Titanium), Zr (Zirconium) and Hf (Hafnium). The transition metals of group Va of the Periodic Table comprise V (Vanadium), Nb (Niobium), and Ta (Tantalum).

In another embodiment, the ceramic is selected from the group consisting of an aluminum ceramic, a silicon ceramic, a titanium ceramic, a vanadium ceramic, a zirconium ceramic, a niobium ceramic, a carbide ceramic, a nitride ceramic, a carbonitride ceramic, an oxide ceramic, and a dioxide ceramic, including any mixture thereof.

Particularly preferred ceramic materials are selected from from the group consisting of aluminum oxide, aluminium silicate, niobium carbide, silicon carbide, silicon nitride, tantalum carbide, titanium carbide, titanium nitride, titanium carbonitride, zirconium oxide, zirconium dioxide, and a mixed oxide of zirconium dioxide and aluminum oxide, including any mixture thereof.

A more preferred ceramic material comprises aluminium oxide, and most preferred, the ceramic material essentially consists of aluminium oxide.

When the heat insulating material comprises a cermet in the form of an alloy comprising a heat-resistant compound and a metal, said heat-resistant compound is preferably selected from the group consisting of a carbide of a transition metal of group IVa of the Periodic Table, a carbide of a transition metal of group Va of the Periodic Table, a nitride of a transition metal of group IVa of the Periodic Table, a nitride of a transition metal of group Va of the Periodic Table, a carbonitride of a transition metal of group IVa of the Periodic Table, and a carbonitride of a transition metal of group Va of the Periodic Table, including any mixture of some or all of the aforementioned compounds.

Any metal may in principle be used in the cermet, and the metal component of the cermet is preferably selected from the group consisting of iron, nickel and cobalt, including any mixture thereof.

The rotary motion of said distal end portion must be sufficient to achieve the result of heat coagulating the soft tissue being contacted by at least said distal end portion in said rotary motion. The rotary motion of said distal end portion is preferably at least about 150,000 rounds per minute and preferably less than about 800,000 rounds per minute, such as at least about 170,000 rounds per minute and preferably less than about 775,000 rounds per minute, for example at least about 190,000 rounds per minute and preferably less than about 750,000 rounds per minute, such as at least about 210,000 rounds per minute and preferably less than about 725,000 rounds per minute, for example at least about 230,000 rounds per minute and preferably less than about 700,000 rounds per minute, such as at least about 250,000 rounds per minute and preferably less than about 700,000 rounds per minute, such as at least about 270,000 rounds per minute and preferably less than about 700,000 rounds per minute, for example at least about 290,000 rounds per minute and preferably less than about 700,000 rounds per minute, such as at least about 310,000 rounds per minute and preferably less than about 700,000 rounds per minute, for example at least about 330,000 rounds per minute and preferably less than about 680,000 rounds per minute, such as at least about 340,000 rounds per minute and preferably less than about 660,000 rounds per minute, for example at least about 350,000 rounds per minute and preferably less than about 640,000 rounds per minut, such as at least about 360,000 rounds per minute and preferably less than about 630,000 rounds per minut, for example at least about 370,000 rounds per minute and preferably less than about 620,000 rounds per minut, such as at least about 380,000 rounds per minute and preferably less than about 610,000 rounds per minut, for example at least about 390,000 rounds per minute and preferably less than about 600,000 rounds per minut, such as at least about 400,000 rounds per minute and preferably less than about 590,000 rounds per minut, for example at least about 410,000 rounds per minute and preferably less than about 580,000 rounds per minut, such as at least about 420,000 rounds per minute and preferably less than about 570,000 rounds per minut, for example at least about 430,000 rounds per minute and preferably less than about 560,000 rounds per minut, such as at least about 440,000 rounds per minute and preferably less than about 550,000 rounds per minut, for example at least about 450,000 rounds per minute and preferably less than about 540,000 rounds per minut, such as at least about 460,000 rounds per minute and preferably less than about 530,000 rounds per minut, for example at least about 470,000 rounds per minute and preferably less than about 520,000 rounds per minut, such as at least about 480,000 rounds per minute and preferably less than about 510,000 rounds per minut, for example about 500,000 rounds per minut.

The distal end portion comprising said heat insulating material is preferably pointed and may form a tip. In particular, when a cutting effect is desired it is preferred that the distal end portion tapers to form a tip.

The device may in one preferred embodiment further comprise a linker portion connecting said distal and proximal ends. The linker portion preferably comprises a cavity for harbouring said distal end portion, and said linker portion may further comprise fixation means for maintaining said distal end portion in a fixed position in said cavity.

In the aspect of the invention pertaining to a method of heat coagulating soft tissue, and comprising the steps of i) providing a device according to the present invention, ii) providing an individual in need of soft tissue treatment, iii) contacting said soft tissue by at least said distal end portion of said device, and iv) heat coagulating said soft tissue by means of said rotary motion of said distal end portion, said heat coagulation in one embodiment effectively reduces the outflow of fluids including fluids comprising blood from said soft tissue. In another preferred embodiment, the heat coagulation essentially eliminates the outflow of fluids including fluids comprising blood from said soft tissue.

The method of heat coagulating soft tissue according to the invention aims to achieve hemostasis and/or results in the achievement of an improved hemostasis. The improved hemostasis is attained for soft tissue comprising vascular tissue, and in particular soft tissue comprising gingival tissue. It is most preferred that the soft tissue essentially consists of gingival tissue.

Furthermore, the invention Comprises a method of obtaining a cutting effect with the device. The cutting effect may be obtained by performing brush stroke movements with the distal end of the device against the soft tissue to be treated. When obtaining the cutting effect the device is not forced against the tissue. When obtaining a cutting effect by the device according to the invention a combination of simultaneous cutting and coagulation is obtained decreasing bleeding and secretion of body fluids from the wound.

The method of heat coagulating soft tissue may further comprise an additional step of cutting or penetrating said soft tissue by using e.g. a conventional cutting instrument such as a scalpel. In a yet further step there is provided a step of eliminating said soft tissue.

In another aspect of the invention, the method of removing gingival tissue by means of treatment and comprising the steps of i) providing a device according to the present invention, ii) providing an individual in need of gingival tissue removal, iii) contacting said gingival tissue by at least said distal end portion of said device, and iv) removing said contacted gingival tissue by means of said rotary motion of said distal end portion of said device, results in a heat coagulation of said soft tissue being contacted under practical circumstances by at least said rotating distal end. The heat coagulation results in an improved hemostasis by at least reducing and/or essentially eliminating the outflow of fluids including blood from said gingival tissue.

In yet another aspect the method of lacerating interradiculary granulation tissue and comprising the steps of i) providing a device according to the present invention, ii) providing an individual in need of interradiculary granulation tissue laceration, iii) contacting said granulation tissue with said distal end portion of said device, and iv) lacerating said interradiculary granulation tissue by means of said rotary motion of said distal end portion of said device, results in a heat coagulation of said interradiculary granulation tissue being contacted under practical circumstances by at least said rotating distal end. The heat coagulation results in an improved hemostasis by at least reducing and/or essentially eliminating the outflow of fluids including blood from said interradiculary granulation tissue.

In one particularly interesting aspect of the invention, there is provided a device according to the present invention for use in one or more of i) a method of heat coagulating soft tissue as described herein above, ii) a method of removing gingival tissue as described herein above, and iii) a method of lacerating interradiculary granulation tissue as described herein above.

One embodiment of the invention pertains to the use of a ceramic drill tip in the manufacture of a device for treatment of soft tissue, wherein said device comprises a distal end portion comprising said ceramic drill tip and a proximal end portion in the form of a non-flexible drill shaft capable of being in operational contact with a power source for generating a rotary motion of said distal end portion, and wherein said rotary motion results in a heat coagulation of said soft tissue being contacted under practical circumstances by at least said rotary distal end comprising said ceramic drill tip.

In yet another embodiment there is provided the use of a ceramic drill tip in the manufacture of a device for treatment of soft tissue, wherein said device comprises a distal end portion comprising said ceramic drill tip and a proximal end portion in the form of a non-flexible drill shaft capable of being in operational contact with a power source for generating a rotary motion of said distal end portion, and wherein said rotary motion results in hemostasis of said soft tissue being contacted under practical circumstances by at least said rotary distal end comprising said ceramic drill tip.

The device according to the invention is described in greater detail in the relation to the drawings.

In FIG. 1, a device 1 according to the invention is shown wherein the distal end portion 2 comprises the heat-insulating material. The distal end portion 2 is preferably provided with a tip 3 of same material. The distal end portion 2 is harboured and fixed in a linker portion 5 connecting the distal end portion 2 to the proximal end portion 4. The length of the device 1 is preferably below 5 cm, such as from 1.5–3.0 cm. The distal end portion 2 preferably constitutes from ¼–½ of the total length of the device 1.

What is claimed is:

1. A device for treatment of soft tissue, said device comprising:
   a distal end portion, the distal end portion comprising a heat-insulating material; and
   a proximal end portion comprising a non-flexible drill shaft, said proximal end portion being connected to the distal end portion such that said distal end portion is rotatable with said proximal end portion, said proximal end portion being adapted to be connected with a power source for generating a rotary motion of said distal end portion,
   wherein said rotary motion of said distal end portion generates friction between said distal end portion and said tissue so as to cause a heat coagulation of said soft tissue that is contacted by at least said rotating distal end.

2. A device according to claim 1, wherein said heat coagulation reduces the outlaw of fluids from said soft tissue.

3. A device according to claim 1 wherein said heat coagulation reduces an outflow of fluids from said soft tissue.

4. A device according to claim 3 wherein said fluids comprise blood.

5. A device according to claim 3 wherein said heat coagulation results in hemostatis.

6. A device according to claim 1 wherein said heat coagulation essentially eliminates an outflow of fluids from said soft tissue.

7. A device according to claim 1 wherein said soft tissue comprises vascular tissue.

8. A device according to claim 7 wherein said vascular tissue comprises mucosal tissue.

9. A device according to claim 8 wherein said mucosal tissue comprises gingival tissue.

10. A device according to claim 1 wherein said heat insulating material consists of a ceramic material characterized by an electrical resistivity essentially making said material electrically nonconductive.

11. A device according to claim 1 wherein said soft tissue consists essentially of gingival tissue.

12. A device according to claim 1 wherein said heat insulating material is selected from the group consisting of a ceramic and a cermet in the form of an alloy comprising a heat-resistant compound and a metal.

13. A device according to claim 12 wherein said heat insulating material comprises a ceramic material.

14. A device according to claim 13 wherein said heat insulating material consists essentially of a ceramic material.

15. A device according to claim 14 wherein said heat insulating material consists of a ceramic material having a Rockwell C hardness of at least 40.

16. A device according to claim 14 wherein said heat insulating material consists of a ceramic material that is essentially thermally nonconductive.

17. A device according to claim 13 wherein said ceramic material comprises aluminum oxide.

18. A device according to claim 17 wherein said ceramic material consists essentially of aluminum oxide.

19. A device according to claim 12 wherein said heat insulating material consists of a ceramic material selected from the group consisting of a carbide of a transition metal of group IVa of the Periodic Table, a carbide of a transition metal of group Va of the Periodic Table, a nitride of a transition metal of group IVa of the Periodic Table, a nitride of a transition metal of group Va of the Periodic Table, a carbonitride of a transition metal of group IVa of the Periodic Table, a carbonitride of a transition metal of group Va of the Periodic Table, an oxide of a transition metal of group IVa of the Periodic Table, and an oxide of a transition metal of group Va of the Periodic Table, including any mixture thereof.

20. A device according to claim 18 wherein said ceramic is selected from the group consisting of an aluminum ceramic, a silicon ceramic, a titanium ceramic, a vanadium ceramic, a zirconium ceramic, a niobium ceramic, a carbide ceramic, a nitride ceramic, a carbonitride ceramic, an oxide ceramic, and a dioxide ceramic, including any mixture thereof.

21. A device according to claim 13 wherein said ceramic material is selected from the group consisting of aluminum oxide, aluminium silicate, niobium carbide, silicon carbide, silicon nitride, tantalum carbide, titanium carbide, titanium nitride, titanium carbonitride, zirconium oxide, zirconium dioxide, and a mixed oxide of zirconium dioxide and aluminum oxide, including any mixture thereof.

22. A device according to claim 12 wherein said heat insulating material comprises a cermet in the form of an alloy comprising a heat-resistant compound and a metal.

23. A device according to claim 12 wherein said heat-resistant compound is selected from the group consisting of a carbide of a transition metal of group IVa of the Periodic Table, a carbide of a transition metal of group Va of the Periodic Table, a nitride of a transition metal of group IVa of the Periodic Table, a nitride of a transition metal of group Va of the Periodic Table, a carbonitride of a transition metal of group IVa of the Periodic Table, and a carbonitride of a transition metal of group Va of the Periodic Table, including any mixture of some or all of the aforementioned compounds, and wherein said metal is selected from the group consisting of iron, nickel and cobalt, including any mixture thereof.

24. A device according to claim 1 wherein said rotary motion is at least about 150,000 rounds per minute and less than about 800,000 rounds per minute.

25. A device according to claim 1 wherein said rotary motion is at least about 290,000 rounds per minute and less than about 700,000 rounds per minute.

26. A device according to claim 1 wherein said rotary motion is at least about 370,000 rounds per minute and less than about 620,000 rounds per minute.

27. A device according to claim 1 wherein said distal end portion comprising said heat insulating material is pointed.

28. A device according to claim 1 wherein said heat insulating material includes a distal part that forms a tip.

29. A device according to claim 1 further comprising a linker portion connecting said distal and proximal end portions.

30. A device according to claim 29 wherein said linker portion comprises a cavity that harbours said distal end portion.

31. A device according to claim 30 further comprising fixation means for maintaining said distal end portion in a fixed position in said cavity.

32. Method of heat coagulation of soft tissue, said method comprising the steps of:

providing a device comprising a proximal end portion and a distal end portion connected to said proximal end portion and rotatable therewith, said distal end portion comprising a heat insulating material;

providing an individual in need of soft tissue treatment, contacting soft tissue of said individual with at least said distal end portion of said device, and rotating said device such that friction between at least said distal end portion of said device and said soft tissue causes heat coagulation of said soft tissue.

33. Method of claim 32 wherein said heat coagulation reduces an outflow of fluids from said soft tissue.

34. Method of claim 32 wherein said heat coagulation essentially eliminates an outflow of fluids from said soft tissue.

35. Method of claim 33 wherein said fluids comprise blood.

36. Method of claim 32 wherein said heat coagulation results in hemostasis.

37. Method of claim 32 wherein said soft tissue comprises vascular tissue.

38. Method of claim 32 wherein said soft tissue comprises gingival tissue.

39. Method of claim 32 wherein said soft tissue consists essentially of gingival tissue.

40. Method of claim 32 wherein said contacting of said soft tissue with at least said distal end portion of said device further comprises a penetration of said soft tissue.

41. Method of claim 40 wherein said penetration of said soft tissue further comprises an elimination of said soft tissue.

42. Method of removing gingival tissue by means of treatment, said method comprising the steps of:

providing a device comprising a proximal end portion and a distal end portion connected to said proximal end portion and rotatable therewith, said distal end portion comprising a heat insulating material;

providing an individual in need of gingival tissue removal, contacting gingival tissue of said individual with at least said distal end portion of said device, and rotating said device such that friction between at least said distal end portion of said device and said gingival tissue removes said gingival tissue by causing heat coagulation of said gingival tissue being contacted.

43. Method of removing hyperplastic gingival tissue by means of treatment, said method comprising the steps of:

providing a device comprising a proximal end portion and a distal end portion connected to said proximal end portion and rotatable therewith, said distal end portion comprising a heat insulating material;

providing an individual in need of hyperplastic gingival tissue removal, contacting hyperplastic gingival tissue of said individual with at least said distal end portion of said device, and rotating said device such that friction between at least said distal end portion of said device and said hyperplastic gingival tissue removes said hyperplastic gingival tissue by causing heat coagulation of said hyperplastic gingival tissue being contacted.

44. Method of modeling gingival tissue by means of treatment, said method comprising the steps of:

providing a device comprising a proximal end portion and a distal end portion connected to said proximal end portion and rotatable therewith, said distal end portion comprising a heat insulating material;

providing an individual in need of gingival tissue modeling, contacting gingival tissue of said individual with at least said distal end portion of said device, and rotating said device such that friction between at least said distal end portion of said device and said gingival tissue models said gingival tissue by causing heat coagulation of said gingival tissue being contacted.

45. Method of lacerating interradiculary granulation tissue, said method comprising the steps of:

providing a device comprising a proximal end portion and a distal end portion connected to said proximal end portion and rotatable therewith, said distal end portion comprising a heat insulating material;

providing an individual in need of interradiculary granulation tissue laceration, contacting granulation tissue of said individual with at least distal end portion of said device, and rotating said device such that friction between at least said distal end portion of said device and said interradiculary granulation tissue lacerates said interradiculary granulation tissue by causing heat coagulation of said tissue being contacted.

46. Method of exposing a tooth at least partly covered by a mucous membrane or mucous lined tissue, said method comprising the steps of:

providing a device comprising a proximal end portion and a distal end portion connected to said proximal end portion and rotatable therewith, said distal end portion comprising a heat insulating material;

providing an individual in need of exposure of a tooth at least partly covered by a mucous membrane or mucous lined tissue, contacting said mucous membrane or mucous lined tissue with at least said distal end portion of said device, and rotating said device such that fiction between at least said distal end portion of said device and said mucous membrane or mucous lined tissue exposes said tooth by causing heat coagulation of said mucous membrane or mucous lined tissue being contacted.

47. Method of exposing an intraosseous implant or part thereof at least partly covered by a mucous membrane or mucous lined tissue, said method comprising the steps of:

providing a device comprising a proximal end portion and a distal end portion connected to said proximal end portion and rotatable therewith, said distal end portion comprising a heat insulating material, providing an individual in need of exposure of an intraosseous implant or part thereof at least partly covered by a mucous membrane or mucous lined tissue, contacting said mucous membrane or mucous lined tissue of said individual with at least said distal end portion of said device, and rotating said device such that friction between at least said distal end portion of said device and said mucous membrane or mucous lined tissue exposes said intraosseus implant or part thereof by causing heat coagulation of said mucous membrane or mucous lined tissue being contacted.

48. Method of cleaning a poche, said method comprising the steps of:

providing a device comprising a proximal end portion and a distal end portion connected to said proximal end portion and rotatable therewith, said distal end portion comprising a heat insulating material;

providing an individual in need of poche cleaning, contacting soft tissue within a poche with said distal end portion of said device, rotating said device such that friction between at least said distal end portion of said device and said soft tissue within said poche cleans said poche by causing heat coagulation of said soft tissue in said poche being contacted.

49. A device for treatment of soft tissue, said device comprising:

a proximal end portion comprising a non-flexible drill shaft;

a power source adapted to produce a rotary motion, said power source being rotatably connected to said proximal end portion;

a distal end portion mounted to an end of said proximal end portion so as to be rotatable with said proximal end portion, said distal end portion comprising a heat-insulating material; wherein said rotary motion generates friction between said distal end portion and said tissue so as to cause heat coagulation of soft tissue that is contacted by at least said distal end.

* * * * *

UNITED STATES PATENT AND TRADEMARK OFFICE
CERTIFICATE OF CORRECTION

PATENT NO. : 6,368,336 B1
DATED : April 9, 2002
INVENTOR(S) : Ronvig

It is certified that error appears in the above-identified patent and that said Letters Patent is hereby corrected as shown below:

Column 4,
Line 58, "$10^{4\ ohm/cm2}$," should read -- $10^4$ ohm/cm$^2$, --

Column 6,
Lines 4, 6, 8, 10, 12, 14, 16, 17, 19, 21, 23, 25, 27 and 29, "per minut," should read -- per minute, --
Line 28, "510,000" should read -- 510,000 --
Line 30, "minut." should read -- minute. --

Column 8,
Line 26, "reduces the outlaw of fluids from said soft tissue." should read -- results in a cutting effect on the soft tissue. --

Column 9,
Line 14, "18" should read -- 12 --

Signed and Sealed this

Sixteenth Day of September, 2003

JAMES E. ROGAN
*Director of the United States Patent and Trademark Office*